US00PP08432P

United States Patent [19]

Cobia

[11] Patent Number: Plant 8,432

[45] Date of Patent: Oct. 19, 1993

[54] CACTUS PLANT 'HOLIDAY SPLENDOR'

[76] Inventor: Barnell L. Cobia, P.O. Box 771369, Winter Garden, Fla. 34777-1369

[21] Appl. No.: 933,818

[22] Filed: Aug. 24, 1992

[51] Int. Cl.[5] ..... A01H 5/00

[52] U.S. Cl. ..... Plt./88.5

[58] Field of Search ..... Plt./88.5

[56] References Cited

U.S. PATENT DOCUMENTS

P.P. 4,196 1/1978 Cobia et al. ..... Plt. 88.5

*Primary Examiner*—James R. Feyrer

*Assistant Examiner*—Erich E. Veitenheimer

*Attorney, Agent, or Firm*—Roger L. Martin

[57] ABSTRACT

A new and distinct plant variety of the Cactaceae family is of the type known commercially as a "Christmas Cactus" and has a growth habit which is similar to that of the "Christmas Charm" variety (U.S. Plant Pat. No. 4,196) but which, nevertheless, differs, among other things, by having phylloclades with thicker and longer midribs, wider wings, and longer teeth, and flowers longer perianth tube with greater major axis dimensions, and a longer basally united group of stamen.

3 Drawing Sheets

BACKGROUND OF THE INVENTION

The invention relates to a new and distinct plant variety of the Cactaceae family and which has been named the *Zygocactus truncatus* 'Holiday Splendor' by the inventor.

Certain plant varieties of the Cactaceae family are well known in the foliage plant market and among these are those which are commonly referred to as the Christmas Cactus varieties because they tend to bloom during the Thanksgiving-Christmas holiday season in the northern hemisphere.

The Christmas Cactus varieties on the market have blooms which vary in color from one variety to the next as is evident from the current U.S. patent art. One of the more popular varieties sold commercially in the market place is the variety that has been named *Zygocactus truncatus* 'Christmas Charm'. The variety has a reddish purple colored bloom and forms the subject matter of U.S. Plant Pat. No. 4,196.

SUMMARY OF THE INVENTION

A general objective has been to develop a new plant variety with a reddish purple colored bloom and which is distinguishable from the "Christmas Charm" variety and capable of being marketed in competition therewith. The objective has been fully realized in the development of the new plant variety hereinafter described in detail. The new plant variety was developed in a nursery located at Winter Garden, Fla., as a hybrid secured by cross-pollinating the flower of an unnamed research variety (ZH19001-T) with the pollen from the flower of yet another unnamed research variety (ZH5311-M1). The seeds taken from the fertilized seed pot (ZH19001-T×ZH5311-M1) were cultivated at the mentioned nursery location and after prolonged observation of the seedlings, the hybridized plant of the new variety was selected and asexually reproduced by propagation of cuttings taken from the original hybrid.

The maternal variety is similar in growth habit and bloom color to the new plant variety. The paternal parent of the new plant variety is less upright than the new variety, and in general, has smaller phylloclades and blooms. The paternal variety also has blooms that can be generally described as less intense in color. Both parents of the new variety are fertile whereas the new plant variety is sterile.

Through successive propagation of cuttings taken from the seedling of the new variety, it has been ascertained that specimens of the new plant variety generally resemble the 'Christmas Charm' variety in most respects but are distinguishable from this variety and from other related varieties known to the inventors by a growth habit which is evident in plant specimens of the new plant variety that have been propagated and grown under nursery conditions utilized in the growing of tropical plants in Winter Garden, Fla., as combining the following principal characteristics:

1. An erect growth habit.
2. Phylloclades which, in comparison to the 'Christmas Charm' variety, have (a) midribs with generally greater length and thickness dimensions, (b) wings with generally greater thickness dimensions, and (c) teeth with generally greater length dimensions.
3. Flowers which, in comparison to the 'Christmas Charm' variety, are sterile and have (a) a perianth tube with generally greater length and major axis dimensions, (b) a tube attached group of stamen that generally have greater length dimensions, and (c) a basally united group of stamen that generally have greater length dimensions.

BRIEF DESCRIPTION OF THE DRAWINGS

The accompanying drawings serve by color photographic means to illustrate the new plant variety and wherein one sheet shows a twelve (12) month old specimen which was grown from the propagation of a single phylloclade in a conventional 3.5" plastic pot (trade designated size) found in the marketplace. A second sheet shows an enlargement of a fully open bloom taken from the specimen shown in the first mentioned sheet. Still another sheet shows a bloom as sectioned generally longitudinally through the perianth tube and ovary to expose the style and stamen arrangement.

DETAILED PLANT DESCRIPTION

The following is a detailed description of the new plant variety with colors and hues, unless otherwise clearly indicated by the text, as for example, through the absence of color notations, being named in accord with the ISCC-NBS Method of Designating Colors (U.S. Department of Commerce, National Bureau of Standards, Circular 553), the named colors being interpreted from color notations derived by comparison with color specimens of the Munsell Book of Color. The description is further based on observations of well fertilized plants about one year old from initial propagation of a single phylloclade and which were grown under 50–75% shaded glass house nursery conditions in the Winter Garden, Fla. area and wherein temperatures range from 60°–85° F. during the winter months, from 75°–95° during the summer months, and are ambient during the intervening periods.

I. Name: *Zygocactus truncatus* 'Holiday Splendor'.

II. Parentage:

A. *Maternal.*—An unnamed and unmarketed fertile research variety that is similar in apparent growth habit to the subject new plant variety.

B. *Paternal.*—An unnamed and unmarketed fertile research variety that is less erect generally smaller foliage and blooms, and bloom colors that are less intense.

III. Classification:

A. *Botanic.*—*Britton and Rose, The Cactaceae,* Constable and Co., Ltd., London 1937, Vol. IV. (1) Family: Cactaceae. (2) Tribe: Cereeae. (3) Sub-Tribe: Epiphyllanae. (4) Genus: Zygocactus. (5) Species: *truncatus* (Haworth) Schumann.

B. *Commercial.*—Thanksgiving-Christmas blooming cactus.

IV. Form: Epiphylic and terrestrial, shade loving, succulent, leafless plant with jointed and branched stems.

V. Stems:

A. *General.*—Irregular with unusually multichotomous branching of both upright and pendulous, adventitiously rootable, flattened phylloclades that have a prominent midrib and prominently toothed lateral wings.

B. *Phylloclades.*—(1) General: Elongated and flat with a tranversely elongated, areole bearing, truncated apex, with inwardly tapering basal wing margins that merge with a usually broadly pointed basal juncture with the phylloclade therebelow, and with an axially located areaole usually being associated with each tooth. (2) Midrib: (a) General — Extends longitudinally of phylloclade and continuously through joints and with a laterally tapering cortex at the wing insertions. Pith surrounding vascular bundles of the vascular system to the marginal teeth. (b) Texture — Smooth, waxy epidermis with wax in small embedded scales and becoming woody in basal stem areas with specimen aging. (c) Size (at maturity) — 1. Length: Usually 24–60 mm. (Avg.=46.1 mm) (Dev.=7.44 mm.) 2. Thickness: Usually 15–10 mm. (Avg.=3.9 mm.) (Dev.=2.28 mm.) (d) Color (at maturity) — Usually dominated by a yellow green and/or an olive green hue. Commonly moderate yellow green (5 GY 5/6) (7.5 GY 5/6), strong yellow green (5 GY 6/8), and/or moderate olive green (7.5 GY 4/6). (3) Wings: (a) General — Dentate and generally flattened from midrib cortex to tooth insertion and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1–2 mm. in the area intermediate the margin and midrib. (Avg.=1.5 mm.) (Dev.=0.36 mm.) 2. Width — Usually 12–23 mm. as measured from phylloclade axis to most offset lateral areole. (Avg.=18.2 mm.) (Dev.=2.69 mm.) 3. Color (at maturity) — Usually dominated by a yellow green and/or an olive green hue. Commonly moderate yellow green (5 GY 5/6) and/or moderate olive green (5 GY 4/4) (7.5 GY 4/6) (7.5 GY 4/4). (4) Teeth: (a) Shape — 1. General: Generally flattened and tapered along the margins and from the wing insertion to an apex having a hyaline, single cell, pointed spine with non-predictable bending. 2. Abaxial margin: Usually straight to convex. 3. Adaxial margin: Usually straight to concave. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 0.75–1.50 mm. in center area. 2. Areole to apex dimension (adaxial marginal side): Usually 6–11 mm. in the upper quadrants of the phylloclades. (Avg.=8.5 mm.) (Dev.=1.92 mm.) (f) Number — Usually 6–9 per phylloclade. (g) Color — Usually dominated by an olive green hue. Commonly moderate olive green (5 GY 4/4) (7.5 GY 4/4) (7.5 GY 4/6). (5) Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axil of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds: Unarmored, ovoid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 5-6. (5) Size (at full bloom): (a) Length (base-tip dimension) — Usually less than 21 mm. (Avg.=10.6 mm.) (Dev.=5.52 mm.) (b) Width (maximum) — Usually less than 15 mm. (Avg.=9.5 mm.) (Dev.=3.10 mm.) (6) Color (at full bloom): Varies from the outer members to the inner members with the smallest outer whorl tepals usually having a marginal blade area that in color is dominated by a reddish purple hue, and a center field and basal area that is dominated by a yellow green hue. The inner whorl tepal members have marginal blade and center field area that in color are dominated by a reddish purple hue that projects into a basal area that in color is dominated by a yellow green hue. Commonly strong reddish purple (2.5 RP 4/10) (2.5 RP 5/10) and/or light reddish purple (2.5 RP 6/8) in marginal and center field areas and brilliant yellow green (2.5 GY 8/8) and/or moderate yellow green (2.5 GY 7/8) in the basal areas of the inner whorl members. Commonly light reddish purple (2.5 RP 6/8) and/or strong reddish purple (2.5 RP 5/10) in marginal blade area and strong yellow green (2.5 GY 6/8) (2.5 GY 7/8) in the basal and center field areas of the outer whorl. (7) Orientation: Erect to recurve at full bloom.

C. *Tube laminating series.*—(1) General: Tepals inserted on ovary and basally united below the throat as outer lamination on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Entire margins with sparse, irregular teeth mainly in apex areas. (3) Texture: Succulent and glabrous outer whorl members and grading inwardly to silken blades with slightly fleshy basal areas. (4) Number: Usually 6-8 tepals. (5) Size: (at full bloom): (a) Length (base-tip dimension) — Usually ranging from about 22 to about 57 mm. (Avg.=38.0 mm.) (Dev.=10.64 mm.) (b) Width (maximum) — Usually ranging from about 13 to about 19 mm. (Avg.=16.3 mm.) (Dev.=1.35 mm.) (6) Color (at full bloom): (a) General — Tepals with a basal area that are dominated by a yellow green hue immediately above insertion in outer members and becoming white in the inner members. Marginal blade and blade center field areas are generally dominated by a reddish purple hue which merges with the distally extending basal area colors. (b) Basal area — White at insertion of inner members and commonly white (2.5 RP 9/0) and/or purplish white (2.5 RP 9/1) and commonly strong yellow green (2.5 GY 7/8) and/or brilliant yellow green (2.5 GY 8/8) at insertion of outer members. (c) Blade are — Commonly strong reddish purple (2.5 RP 5/10) (2.5 RP 4/10) (10 P 5/10). (7) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and elipsoidal in cross section with the major ellipsoidal axis usually generally normal to the plane of the supporting phylloclade. (b) Blades — Nearly zygomorphic and thinly spatulate with acute tips and entire margins having sparse irregular teeth in apex area. (c) Carina (keel) — Irregular and transcending. (3) Texture: (a) Perianth Tube — Thick, succulent and slightly ribbed. (b) Blades — Translucent and silken. (c) Carina (keel) — Fleshy. (4) Number: Usually 8-9. (5) Size (at fully bloom): (a) Perianth tube — 1. Length (base-keel): Usually 32-36 mm. along tube axis. (Avg.=34.2 mm.) (Dev.=1.40 mm.) 2. Major Axis: Usually 10-15 mm. at throat interior. (Avg.=12.8 mm.) (Dev.=1.85 mm.) 3. Minor Axis: Usually 6-9 mm. at throat interior. (Avg.=7.6 mm.) (Dev.=0.92 mm.) (b) Blades — 1. Length (keel-tip): Usually 27-32 mm. (Avg.=29.9 mm.) (Dev.=1.30 mm.) 2. Width (maximum): Usually 12-16 mm. (Avg.=14.0 mm.) (Dev.=0.89 mm.) (6) Color (at full bloom): (a) Perianth Tube — A basic field that is generally translucent and white with longitudinally extending, randomly arranged striations or streaks that in color are commonly purplish white (5 RP 9/1). The basic field is translucent and white (2.5 RP 9/0). (b) Blades — A continuous marginal and center blade area distally of the keel that in color is dominated by a reddish purple hue and which merges with a basal area distally of the keel that is usually translucent and white. Commonly strong reddish purple (2.5 RP 5/10) (2.5 RP 4/10) (10 P 5/10) in the continuous marginal and center blade areas. Commonly white (2.5 RP 9/0) and/or purplish white (2.5 RP 9/1) in the basal area distally of the keel. (c) Carina (keel) — Commonly white (2.5 RP 9/0) and/or purplish white (2.5 RP 9/1). (7) Orientation: Acute to recurve.

E. *Androecium (stamens).*—(1) General: Numerous exerted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 76-90. (b) Basally united group — Usually 19-24. (3) Filaments: (a) General — Translucent with anther connective. (b) Shape — Long, slender, terete. (c) Texture — Glabrous and capillaceous. (d) Color — Usually dominated by a purplish white and/or purplish pink hue in the distal area and becoming white and/or purplish white in the basal area. Commonly purplish white (5 RP 9/2), pale purplish pink (5 RP 9/2) and/or light purplish pink (5 RP 8/6) in the distal area and commonly purplish white (5 RP 9/1) and/or white (2.5 RP 9/0) in the basal area. (e) Size (at full bloom) — 1. Length: a. Tube attached group — Usually 40-60 mm. (Avg.=52.8 mm.) (Dev.=6.27 mm.) b. Basally united group — Usually 37-53 mm. (Avg.=43.8 mm.) (Dev.=5.29 mm.) 2. Diameter: Usually about 0.25-0.50 mm. intermediate opposite ends. (4) Anthers: (a) General — Adnate with four longitudinally dehiscent pollen sacs and connective inserted at end. (b) Shape — Elongated. (c) Texture — Waxy. (d) Color (before dehiscence) —

Dominated by an orange yellow hue. Commonly pale orange yellow (10 YR 9/4) (10 YR 8/4) (10 YR 8/6), light orange yellow (10 YR 8/6) and/or moderate orange yellow (10 YR 8/6). (e) Sterility — Sterile.

F. *Gynoecium* (*pistil*).—(1) General: Exerted and compound, parietal placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by white at the basal end and progressively varying to a color dominated by a reddish purple hue at the distal end. Commonly white (2.5 RP 9/0) at basal end and strong reddish purple (2.5 RP 5/10) (2.5 RP 4/10) at the distal end. (e) Size (at full bloom) — 1. Length: Usually 60–64 mm. (Avg.=61.7 mm.) (Dev.=1.50 mm.) 2. Diameter: Usually 1.0–1.25 mm. intermediate opposite ends. (3) Stigma: (a) General — Exerted and erect with usually 6–7 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by a purplish pink and/or reddish purple hue. Commonly moderate purplish pink (2.5 RP 7/6), light reddish purple (2.5 RP 6/8) and/or strong reddish purple (2.5 RP 5/10). (e) Size — 1. Length: Usually 5–6 mm. along inner margins. (4) Ovary: (a) General — Inferior with thin epidermis and usually 5–7 carpels with numerous ovules. (b) Shape — Terete to ovoid and generally broadening from insertion to floral end. (c) Texture — Succulent with glabrous thin outer epidermis. (d) Color — A basic field with color usually dominated by a yellow green hue. Commonly strong yellow green (2.5 GY 6/8) (2.5 GY 7/8) and/or moderate yellow green (2.5 GY 6/6) (2.5 GY 5/6). (e) Size — 1. Length: Usually 10–11 mm. from insertion to cavity base. (Avg.=10.3 mm.) (Dev.=0.46 mm.) 2. Major axis: Usually 9–11 mm. at distal end of concavity. (Avg.=9.6 mm.) (Dev.=0.88 mm.) 3. Minor axis: Usually 7–9 mm. at distal end of concavity. (Avg.=8.0 mm.) (Dev.=0.58 mm.).

VIII. Growth habit: Erect.

General Description of a Plant Specimen

Age of Plant: Twelve (12) months from initial propagation of single phylloclade.

Branches from propagated phylloclade: Four (4).

Total number of new phylloclades grown: Thirty eight (38).

GENERAL:

| Branch Number | Number of Phylloclades | Maximum Length | Number of Tips |
|---|---|---|---|
| 1 | 3 | 44 mm. | 2 |
| 2 | 21 | 58 mm. | 6 |
| 3 | 12 | 59 mm. | 3 |
| 4 | 2 | 37 mm. | 1 |

MIDRIBS:

| Branch Number | Average Midrib Length | Average Midrib Thickness |
|---|---|---|
| 1 | 33.3 mm. | 2.2 mm. |
| 2 | 46.1 mm. | 4.1 mm. |
| 3 | 46.6 mm. | 4.1 mm. |
| 4 | 34.5 mm. | 1.8 mm. |

WINGS:

| Branch Number | Average Wing Center Thickness | Average Wing Width (Maximum) |
|---|---|---|
| 1 | 1.5 mm. | 14.0 mm. |
| 2 | 1.8 mm. | 18.3 mm. |
| 3 | 1.7 mm. | 18.2 mm. |
| 4 | 1.3 mm. | 14.0 mm. |

TEETH:

| Branch Number | Teeth (Avg.) Per Phylloclade | Average Tooth Center Thickness | Average Areole To Apex Length |
|---|---|---|---|
| 1 | 5.7 | 1.0 mm. | 7.5 mm. |
| 2 | 7.4 | 1.0 mm. | 9.0 mm. |
| 3 | 7.3 | 1.0 mm. | 8.5 mm. |
| 4 | 6.5 | 1.0 mm. | 8.0 mm. |

PHYLLOCLADE COLOR: Moderate yellow green (5 GY 5/6), strong yellow green (5 GY 6/8), and moderate olive green (7.5 GY 4/6)(7.5 GY 4/4)(5 GY 4/4).

General Description of a Flower

The following is a general description of a flower of the new plant variety and which bloomed in December on a 12 month old plant specimen grown under shaded greenhouse nursery conditions in Winter Graden, Fla.

Number of buds and blooms on plant specimen: 14.

Bloom life: 8 days.

Sepaloid series of tepals:

*Number.*—5.

*Tepal size* (*at full bloom*).—Maximum base-tip dimension: 18 mm. Minimum base-tip dimension: 5 mm. Maximum width dimension: 14 mm.

*Color* (*at full bloom*).—Strong reddish purple (2.5 RP 4/10) (2.5 RP 5/10) and light reddish purple (2.5 RP 6/8) in marginal and center field areas and brilliant yellow green (2.5 GY 8/8) in the basal areas of the inner whorl members. Light reddish purple (2.5 RP 6/8) and strong reddish purple (2.5 RP 5/10) in marginal blade area and strong yellow green (2.5 GY 6/8) (2.5 GY 7/8) in the basal and center field areas of outer whorl members.

Tube laminating series of tepals:

*Number.*—8.

*Size* (*at full bloom*).—Maximum base-tip dimension: 55 mm. Minimum base-tip dimension: 24 mm. Maximum blade width: 18 mm. Minimum blade width: 16 mm.

*Color* (*at full bloom*).—White (2.5 RP 9/0) at insertion of inner members and strong yellow green (2.5 GY 7/8) and brilliant yellow green (2.5 GY 8/8) in insertion of outer members. Strong reddish purple (2.5 RP 5/10) (2.5 RP 4/10) (10 P 5/10) in marginal and center field areas of inner and outer members.

Tube forming series of tepals:

*Number.*—9.

*Size* (*at full bloom*).—Perianth tube: Length (base to keel) — 36 mm. along the tube axis. Major axis — 13 mm. at throat interior. Minor axis — 8 mm. at throat interior. Blades: Maximum length (keel-tip) — 31 mm. Minimum length (keel-tip) — 29 mm. Maximum blade width — 16 mm. Minimum blade width — 15 mm.

*Color.*—Perianth tube: A basic field of white (2.5 RP 9/0) with random striations of purplish white (2.5 RP 9/1). Blades: White (2.5 RP 9/0) in basal areas distally of the keel and strong reddish purple (2.5 RP 5/10) (2.5 RP 4/10) (10 P 5/10) in the continuous marginal and center field area of the blades.

Androecium:

*Stamen number.*—Tube attached group: 83. Basally united group: 21.

*Filaments.*—Color: Purplish white (5 RP 9/2), pale purplish pink (5 RP 9/2), and light purplish pink (5 RP 8/6) in the distal area and purplish white (5 RP 8/6) in the basal area.

*Size (at full bloom).*—Length — Tube attached grup: 55 mm (avg). Basally united group: 42 mm. (avg). Diameter: About 0.30 mm. intermediate the opposite ends.

*Anthers.*—Color (before dehiscing): Pale orange yellow (10 YR 8/4) (10 YR 8/6), light orange yellow (10 YR 8/6), and moderate orange yellow (10 YR 8/6).

Gynoecium (pistil):

*Style.*—Color: White (2.5 RP 9/0) in basal area and strong reddish purple (2.5 RP 5/10) (2.5 RP 4/10) in distal area. Size (at full bloom): Length — 64 mm. Diameter — 1.0 mm. Stigma — Color: Moderate purplish pink (2.5 RP 7/6) and light reddish purple (2.5 RP 6/8). Size: 6 mm. (avg) lobe length. Ovary — Color: Strong yellow green (2.5 GY 6/8) (2.5 GY 7/8) and moderate yellow green (2.5 GY 6/6). Size (at full bloom): Length (insertion to concavity base) — 11 mm. Major axis — 10 mm. at distal end of concavity. Minor axis — 8 mm. at distal end of concavity.

We claim:

1. A new and distnact plant variety of the Cactaceae family as shown and described and which is mainly distinguished from its antecedents and known related varieties by growth characteristics that are similar to those of the "Christmas Charm" variety but as modified by the combination of the following characteristics:

(1) A more erect posture at maturity than the "Christmas Charm" variety;

(2) Phylloclades which, in comparison to the "Christmas Charm" variety have (a) midribs with generally greater length and thickness dimensions, (b) wings with generally greater thickness dimensions, and (c) teeth with generally greater length dimensions;

(3) Flowers which, in comparison to the "Christmas Charm" variety, have (a) a perianth tube with generally greater length and major axis dimensions, (b) a tube attached group of stamen that generally have greater length dimensions, and (c) a basally united group of stamen that generally have greater length dimensions.

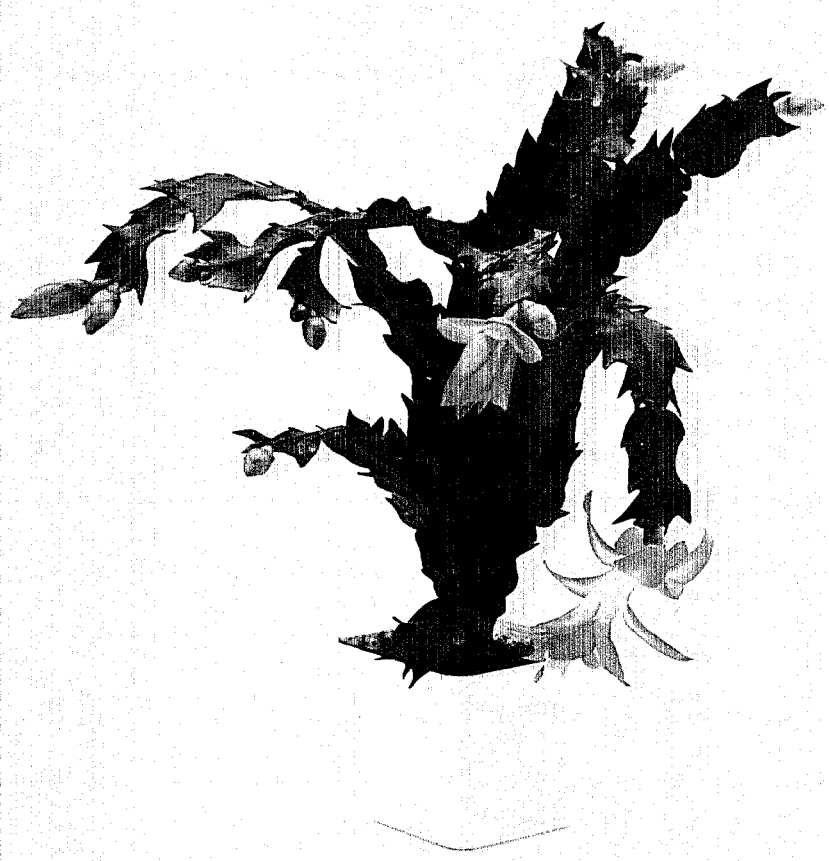

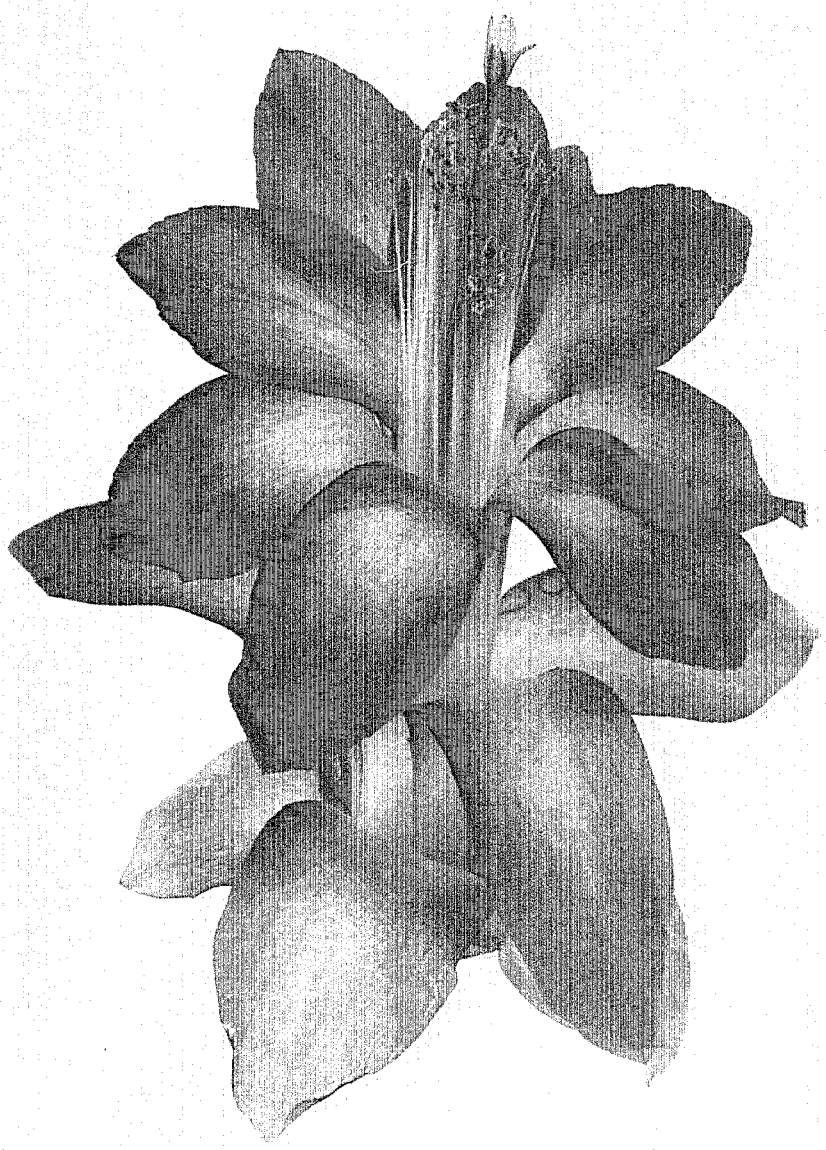

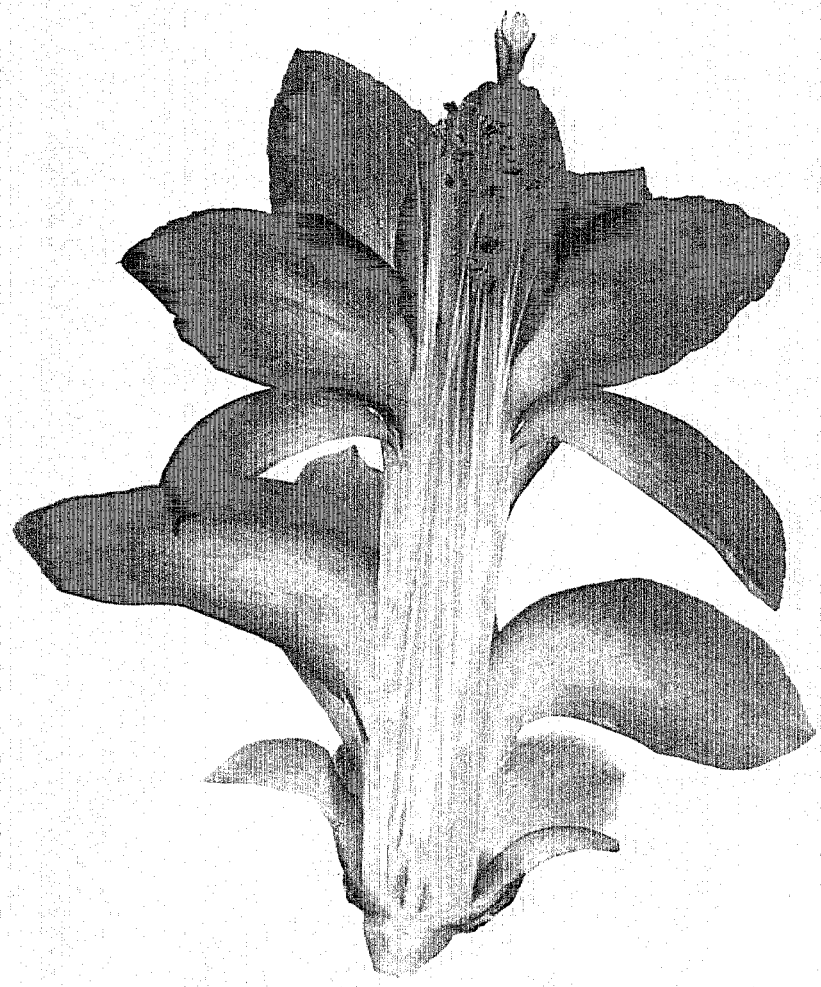

* * * * *